United States Patent
Knauf et al.

(10) Patent No.: US 9,284,256 B2
(45) Date of Patent: Mar. 15, 2016

(54) PROCESS FOR THE PRODUCTION OF NITROBENZENE BY ADIABATIC NITRATION

(71) Applicant: Bayer MaterialScience AG, Leverkusen (DE)

(72) Inventors: Thomas Knauf, Dormagen (DE); Michael Merkel, Dusseldorf (DE)

(73) Assignee: Bayer MaterialScience AG, Leverkusen (DE)

( * ) Notice: Subject to any disclaimer, the term of this patent is extended or adjusted under 35 U.S.C. 154(b) by 0 days.

(21) Appl. No.: 14/415,794

(22) PCT Filed: Jul. 23, 2013

(86) PCT No.: PCT/EP2013/065506
§ 371 (c)(1),
(2) Date: Jan. 20, 2015

(87) PCT Pub. No.: WO2014/016292
PCT Pub. Date: Jan. 30, 2014

(65) Prior Publication Data
US 2015/0166460 A1    Jun. 18, 2015

(30) Foreign Application Priority Data
Jul. 27, 2012 (EP) .................... 12178161

(51) Int. Cl.
*C07C 201/00* (2006.01)
*C07C 201/08* (2006.01)
*C07C 201/16* (2006.01)

(52) U.S. Cl.
CPC ............ *C07C 201/08* (2013.01); *C07C 201/16* (2013.01)

(58) Field of Classification Search
CPC ......................... C07C 201/06; C07C 201/08
USPC ........................................ 568/939
See application file for complete search history.

(56) References Cited

U.S. PATENT DOCUMENTS

| 2,256,999 | A | 9/1941 | Castner |
| 4,091,042 | A | 5/1978 | Alexanderson et al. |
| 5,313,009 | A | 5/1994 | Guenkel et al. |
| 5,616,818 | A | 4/1997 | Pirkl et al. |
| 5,763,697 | A | 6/1998 | Hermann et al. |
| 7,326,816 | B2 | 2/2008 | Knauf et al. |
| 7,344,650 | B2 | 3/2008 | Knauf et al. |
| 7,763,759 | B2 | 7/2010 | Knauf et al. |
| 2010/0280271 | A1 | 11/2010 | Sommer et al. |
| 2011/0196177 | A1* | 8/2011 | Munnig et al. ............... 568/939 |
| 2013/0204043 | A1 | 8/2013 | Knauf et al. |

FOREIGN PATENT DOCUMENTS

| DE | 1129466 | 5/1962 |
| DE | 102009005324 A1 | 7/2010 |
| EP | 0373966 A2 | 6/1990 |
| EP | 0436443 A2 | 7/1991 |
| EP | 0976718 A2 | 2/2000 |
| EP | 1132347 A2 | 9/2001 |
| EP | 20155655 B1 | 8/2011 |
| WO | 2010051616 A1 | 5/2010 |

* cited by examiner

*Primary Examiner* — Sikarl Witherspoon
(74) *Attorney, Agent, or Firm* — Donald R. Palladino

(57) ABSTRACT

The present invention provides a continuous process for the production of nitrobenzene by nitration of benzene with mixtures of sulfuric and nitric acid using a stoichiometric excess of benzene, in which the content of aliphatic organic compounds in the feed benzene during the start-up period of the production plant is always maintained at less than 1.5 wt. %, based on the total mass of the feed benzene. This is achieved either by mixing the feed benzene comprising recycled unreacted benzene (recycled benzene) and benzene newly supplied to the reaction (fresh benzene) in appropriate quantitative ratios during the start-up period, depending on the purity of the two streams, or by completely omitting the recycling of unreacted benzene during the start-up period, i.e. the feed benzene consists only of benzene newly supplied to the reaction.

10 Claims, 1 Drawing Sheet

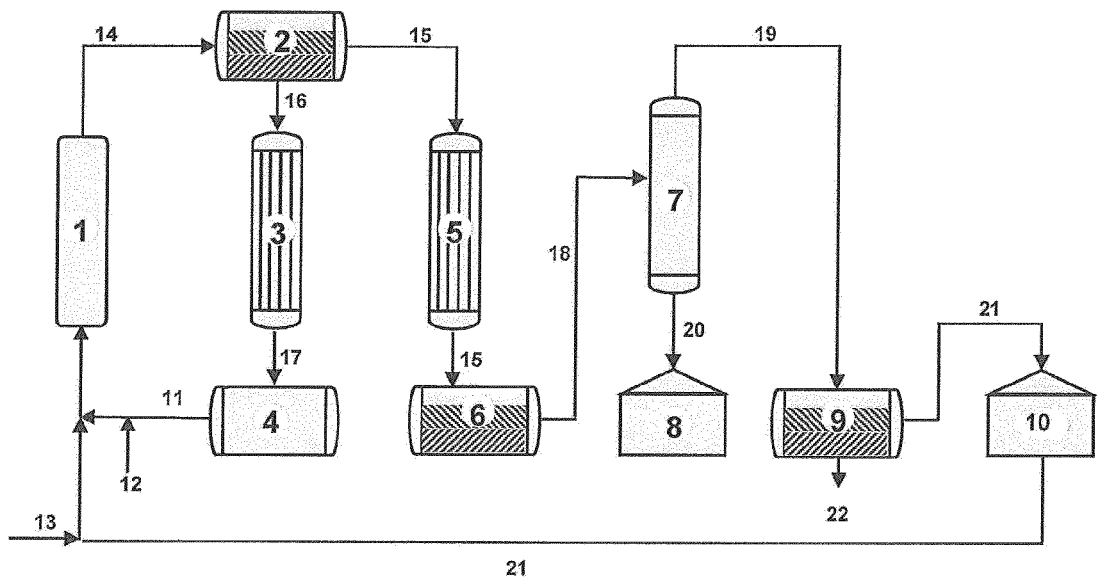

PROCESS FOR THE PRODUCTION OF NITROBENZENE BY ADIABATIC NITRATION

CROSS-REFERENCE TO RELATED APPLICATIONS

This application is a National Phase Application of PCT/EP2013/065506, filed Jul. 23, 2013, which claims priority to European Application No.: 12178161.1, filed Jul. 27, 2012, each of which being incorporated herein by reference.

FIELD

The present invention provides a continuous process for the production of nitrobenzene by nitration of benzene with mixtures of sulfuric and nitric acid using a stoichiometric excess of benzene, in which the content of aliphatic organic compounds in the feed benzene during the start-up period of the production plant is always maintained at less than 1.5 wt. %, based on the total mass of the feed benzene. This is achieved either by mixing the feed benzene comprising recycled unreacted benzene (recycled benzene) and benzene newly supplied to the reaction (fresh benzene) in appropriate quantitative ratios during the start-up period, depending on the purity of the two streams, or by completely omitting the recycling of unreacted benzene during the start-up period, i.e. the feed benzene consists only of benzene newly supplied to the reaction.

BACKGROUND

The present invention relates to a continuous process for the production of nitrobenzene by adiabatic nitration of benzene by a mixture of sulfuric and nitric acid (so-called mixed acid). A process of this type was first claimed in U.S. Pat. No. 2,256,999 and is described in more modern embodiments in U.S. Pat. Nos. 4,091,042, 5,313,009 and 5,763,697.

Common to the adiabatic processes described is the fact that the starting substances benzene and nitric acid are reacted in a large excess of sulfuric acid, which takes up the heat of reaction liberated and the water formed during the reaction.

The reaction route generally involves combining the nitric acid and sulfuric acid to form so-called nitrating acid (also known as mixed acid). Benzene is metered into this nitrating acid. The reaction products are substantially water and nitrobenzene. In the nitration reaction, benzene is used at least in a stoichiometric quantity, based on the molar quantity of nitric acid, but preferably in a 2% to 10% excess. The crude nitrobenzene formed in the reaction apparatus and separated off from the acid phase in the phase separation apparatus is subjected to washing and a work-up by distillation according to the prior art, as described for example in EP 1 816 117 A1 (page 2, lines 26 to 42), U.S. Pat. No. 4,091,042 (see above) or U.S. Pat. No. 5,763,697 (see above). It is characteristic of this work-up that unreacted excess benzene is separated from nitrobenzene in a final distillation after the wash and reused in the nitration reaction as recycled benzene, which also comprises low-boiling, non-aromatic organic compounds (so-called low boilers) (cf. DE 10 2009 005 324 A1). The treatment of the exhaust gas from the adiabatic nitration reaction is described in EP 0 976 718 B1. The exhaust gas of circulating acid and finished crude nitrobenzene is drawn off, combined and sent through an NOx absorber to recover dilute nitric acid, which can be returned into the reaction. The sulfuric acid referred to as circulating acid is concentrated in a flash evaporator and freed from organics as far as possible. High-boiling organics, such as e.g. nitrobenzene, dinitrobenzene and nitrophenols, remain in the circulating acid in traces and are therefore also returned to the reaction.

The quality of an adiabatic process for the nitration of aromatic hydrocarbons is defined on the one hand by the product's content of undesired by-products of the reaction, which are formed by multiple nitration or oxidation of the aromatic hydrocarbon or of the nitroaromatic. The aim in the production of nitrobenzene is to minimise the content of dinitrobenzene and of nitrophenols, in particular of trinitrophenol (picric acid), which is classified as explosive. On the other hand, the quality of an adiabatic process is defined by the ability of the process to be operated without any industrial production losses.

In order to obtain nitrobenzene with particularly high selectivities, the nature of the mixed acid to be used has been specified in detail (EP 0 373 966 B1, EP 0 436 443 B1 and EP 0 771 783 B1), and it has been pointed out that the content of by-products is determined by how high the maximum temperature is (EP 0 436 443 B1, column 15, lines 22 to 25). It is also known that a high initial conversion is advantageous for high selectivity and that this is achieved if optimum mixing is effected at the beginning of the reaction (EP 0 771 783 B1, paragraph [0014]).

Excellent selectivities are achieved if the initial reaction temperature is selected to be very low (WO2010/051616 A1), but this equates to a much longer reaction period. A high space-time yield is advantageous for the industrial application of a process, since this enables compact reaction equipment to be constructed which is distinguished by a low investment volume relative to capacity. This approach is therefore counter-productive.

It is common to all of the literature references cited that they do not describe the start-up process of a nitration plant and its difficulties.

With regard to the quality of the feed substance benzene on the adiabatic production of nitrobenzene, EP 2 246 320 A1 describes that commercially available benzene can be contaminated to a greater or lesser degree depending on its source. Typical impurities are other aromatics, in particular toluene and xylene, which can be comprised in benzene of standard purity in a quantity of up to 0.05 wt. % in each case. Other typical impurities for benzene are non-aromatic organic compounds, which can constitute a total of up to 0.07 wt. %. Cyclohexane (up to 0.03 wt. %) and methylcyclohexane (up to 0.02 wt. %) are mentioned in particular here. The impurities described above in the concentrations mentioned have either no negative effect at all in the subsequent steps in the process chain for the production of di- and polyisocyanates of the diphenylmethane series (MDI) or only a slight one, for example by minimally increasing the difficulty of waste water and exhaust air treatment in the nitrobenzene process as a result of non-aromatic organics in the benzene. Costly purification of benzene for use in the MDI process chain is therefore considered disproportionate and can be omitted. EP 2 246 320 A1 does not go into the non-aromatic organic compounds in the benzene that has been separated off from the crude product after completion of the reaction and returned into the nitration (so-called "recycled benzene").

DE 10 2009 005 324 A1 discloses that technical benzene generally has a proportion of low-boiling non-aromatic organic compounds (low boilers) of 0.01 to 0.5%. In the common processes of benzene nitration, however, it is not technical benzene as such that is used but a mixture of recycled benzene and technical benzene, so that the content of low boilers in the benzene actually used can be considerably higher than in commercially available technical benzene. DE 10 2009 005 324 A1 discloses a value of 5% by way of example (section [0007]). According to the teaching of this document, such a high proportion of low boilers in the actual nitration is still not disadvantageous. DE 10 2009 005 324 A1 only goes into problems with the subsequent phase separation (section [0008]). To solve these problems, a special phase separation process is proposed, using a pressure-maintaining siphon.

EP 2 155 655 B1 only goes into aromatic impurities (alkyl-substituted aromatics) in benzene.

DE-AS-1 129 466 describes a process for the mononitration of technical benzene, xylene and toluene, which have the conventional contents of aliphatic hydrocarbons, in which the first runnings of unreacted aromatic compound formed in the distillation of the nitroaromatic compound, which are rich in aliphatic impurities, are mixed with fresh aromatic compound, supplied to the nitration and the newly formed first runnings are circulated as often as desired. (In the case of benzene as the starting substance, the aromatic first runnings in this document correspond to the above-mentioned recycled benzene.) The person skilled in the art therefore takes from this document the technical teaching that a relatively high proportion of aliphatic impurities in the aromatic compound to be used has no negative effect on nitration.

It is true that the processes of the prior art described succeed in producing a nitrobenzene having a low content of by-products, i.e. comprising only from about 100 ppm to 300 ppm of dinitrobenzene and 1500 ppm to 2500 ppm of nitrophenols, with picric acid possibly making up a proportion of 10 wt. % to 50 wt. % of the nitrophenols. The processes are also distinguished by a high space-time yield.

However, only processes which are already in progress are described, i.e. in which the period from the beginning of the reaction to achieving the target load (so-called "start-up period") has already passed. Any particular difficulties during start-up of an adiabatic nitration process are not mentioned.

BRIEF DESCRIPTION OF THE DRAWINGS

FIG. 1 is a flow diagram of a nitrobenezene production process according to the Examples.

DETAILED DESCRIPTION

The starting point for the present invention was the finding that impurities in the starting substances, in particular impurities in the benzene feed (i.e. according to the prior art a mixture of fresh benzene of technical purity and recycled benzene), have a negative effect on the process to a particular degree during the start-up period.

Impurities in the freshly supplied benzene and/or in the recycled benzene reduce the overall concentration of benzene available. As a result, the reaction is slowed down, which has a particularly critical effect during the start-up period when the final reaction temperature has not yet been reached and therefore the rate of reaction is reduced in any case compared with the state of a plant that has been run in. The reduced benzene concentration can lead to the use of too great a quantity of nitric acid. This in turn increases the quantity of undesirable polynitrated products and NOx gases. The latter gives rise to the formation of other by-products. Critical impurities in this sense are in particular aliphatic organic compounds (low boilers, see above). These can outgas during the reaction together with NOx gases, thus causing further disadvantages, such as e.g. poorer mixing of the reactants and a reduced reaction volume.

Taking the above into account, the present invention provides a process for the production of nitrobenzene in which particular attention is paid to the critical period of the start-up of the reaction. In particular, it has been found that, by limiting the content of aliphatic organic compounds in the benzene actually used, at least during the start-up period, the above-mentioned difficulties are overcome or at least significantly reduced. This limiting of the content of aliphatic organic compounds in the benzene actually used, at least during the start-up period, can be achieved in various ways, which are provided by the present invention.

In particular, the present invention provides a continuous process for the production of nitrobenzene by nitration of benzene, in which a) a benzene-comprising stream (a.1), which encompasses at least 90 wt. %, preferably at least 95 wt. % and particularly preferably at least 99 wt. % benzene, based in each case on the total mass of (a.1), is reacted in a reactor with a mixture of sulfuric acid (a.2) and nitric acid (a.3) under adiabatic conditions, benzene being used in a stoichiometric excess based on nitric acid (a.3) of preferably 2.0% to 20%, particularly preferably of 5.0% to 10% of the theoretical value, and the quantity M' of the benzene-comprising stream (a.1) supplied to the reactor per hour being increased within a period t from the beginning of the nitration until a preset target value for M' is achieved, b) the process product obtained in step a) is separated into an aqueous phase encompassing sulfuric acid (b.1) and an organic phase encompassing nitrobenzene (b.2), c) the aqueous phase (b.1) obtained in step b) is concentrated by evaporation of water to form an aqueous phase (c.1) with an increased sulfuric acid concentration compared with (b.1), and the phase (c.1) being partially to completely returned into step a) and used as a component of (a.2), d) the organic phase (b.2) obtained in step b) is worked up to form pure nitrobenzene (d.1), preferably by washing with aqueous media and subsequent rectification, a benzene-comprising stream (d.2) being obtained (the so-called "recycled benzene"), which preferably encompasses 40.0 wt. % to 99.9 wt. %, particularly preferably 60.0 wt. % to 99.9 wt. %, most particularly preferably 80.0 wt. % to 99.9 wt. % benzene, based in each case on the total mass of (d.2), and which is partially to completely returned into step a) and used as a component of (a.1), the recirculation of (d.2) optionally being omitted during the period t, and in which, at least during the period t, only a benzene-comprising stream (a.1) having a content of aliphatic organic compounds of less than 1.5 wt. %, preferably of less than 0.50 wt. %, particularly preferably of less than 0.20 wt. %, most particularly preferably of less than 0.10 wt. %, based in each case on the total mass of (a.1), is supplied to the reactor.

The benzene excess based on nitric acid of 2.0% to 20%, preferably of 5.0% to 10% of the theoretical value, relates to the molar ratio of benzene and nitric acid. Theoretically, one mole of nitric acid reacts with one mole of benzene to form one mole of nitrobenzene.

It is known to the person skilled in the art that a continuously operated industrial process starting from a production plant which is not in operation (e.g. after a stoppage for maintenance) cannot immediately be ramped back up to the process parameters from before the production stoppage. Feeds and apparatus have to be heated up, apparatus may have to be rendered inert and the loading of the apparatus with the feeds is gradually increased up to the desired target value. If a production plant for the production of nitrobenzene is to be operated at a target loading $M'_{target}$ of x [kg(benzene)/h], this target loading can be achieved, for example, by initially adjusting the loading M' at the beginning of the nitration to a value of 0.25 x and then increasing the loading within 4 hours, via the intermediate steps M'=0.50 x and M'=0.75 x, to the value M'=x=M'$_{target}$. Alternatively, from a particular starting value, e.g. M'=0.50 x, a continuous load increase to M'=x can be implemented. These examples of course only represent examples of a large number of possible start-up procedures, the precise configuration of which depends on the specific conditions of a production plant and cannot therefore be generalised. A common feature of all conceivable start-up procedures, however, is that only after a period t has passed is the desired target loading of x achieved. This period t is referred to according to the invention as the start-up period. During the start-up period, the mass flow of nitric acid (a.3) being supplied continuously to the reactor is, of course, adjusted to the respective mass flow of benzene-comprising stream (a.1), i.e. at the beginning of the start-up period, when only a fraction of the desired target loading of benzene M'$_{target}$ is being supplied to the reactor, only a corresponding fraction of nitric acid is also supplied to the reactor. Preferably during the start-up period t, the same percentage excess of benzene, based on nitric acid, is maintained as after reaching the target loading M'$_{target}$. The mass ratio of nitric acid (a.3) to sulfuric acid (a.2) can differ during the start-up period from that after reaching the target loading of benzene M'$_{target}$; in particular, it can be lower. In particular, it is preferred to supply only sulfuric acid (a.2) to the reactor initially and to supply nitric acid (a.3) and benzene-comprising stream (a.1) only after reaching a stable operating state of the sulfuric acid circulation.

Aliphatic organic compounds within the meaning of the present invention preferably encompass cyclohexane, heptane, methylcyclohexane, bicycloheptane, isomers of dimethylcyclopentane, ethylcyclopentane, pentane, cyclopentane and 2-methylhexane. According to the invention, the content of aliphatic organic compounds in the benzene-comprising stream (a.1) (the so-called "feed benzene") must be monitored. For this purpose, analytical measurements are necessary. Measurements are taken of the fresh benzene in the tank, the feed benzene and the recycled benzene (d.2), preferably by taking samples at the appropriate points and analysing the samples by gas chromatography. Other methods of determination (e.g. spectroscopic methods), optionally also online or inline, can also be used in principle, although these are not preferred. However, the value determined by gas chromatography is the definitive value for the upper limit according to the invention of the content of organic aliphatic compounds. The analysis of the stream (d.2) takes place in a preferred embodiment, namely the work-up by rectification, at the head of the rectifying column.

The word "a/an" within the framework of this invention in connection with countable parameters is to be understood as an indication of number only if this is expressly stated. For example, the expression "a reactor" does not exclude the possibility of the presence of more than one reactor (connected in series or in parallel).

It is essential to the invention that the content of aliphatic organic compounds in the benzene-comprising stream (a.1) (the so-called "feed benzene") corresponds to the above-mentioned concentrations at least during the start-up period t. This goal can be achieved in alternative ways:

In a first variant, the partial to complete recirculation of the benzene-comprising stream (d.2) also takes place during the start-up period. In this case, the feed benzene during the entire nitration process is a mixture of fresh benzene of technical purity (the so-called "fresh benzene") and the recirculated benzene-comprising stream (d.2) (the so-called "recycled benzene"). At least during the start-up period, the benzene excess in step a) and the ratio of fresh benzene to recycled benzene should be adjusted as a function in particular of the purity of the recycled benzene so that the required maximum content of aliphatic organic compounds in the feed benzene of less than 1.5 wt. %, preferably of less than 0.50 wt. %, particularly preferably of less than 0.20 wt. %, most particularly preferably of less than 0.10 wt. %, based in each case on the total mass of the feed benzene (a.1), is not exceeded. In principle, of course, the purity of the available fresh benzene should also be taken into account. In general, however, this is available in such purity that the main focus should be on the recycled benzene.

In a second variant, the partial to complete recirculation of the benzene-comprising stream (d.2) (the so-called "recycled benzene") takes place only after the start-up period has passed. In this case, the feed benzene during the start-up period consists of fresh benzene of technical purity (the so-called "fresh benzene"), and only after the start-up period has passed is a mixture of fresh benzene and recycled benzene used as feed benzene. While it is true that this variant has the disadvantage that the recycled benzene cannot be recycled into the process during the start-up period, however, it is technically simpler to implement because the adjustment of the benzene excess in step a) and of the ratio of fresh to recycled benzene as a function of the purity of the recycled benzene in particular can be omitted. Since commercially available fresh benzene generally has a content of aliphatic organic compounds which meets the requirements according to the invention, this can usually be used directly. However, if only fresh benzene is available having a purity that fails to meet the requirements according to the invention, this must be purified before being used in step a), preferably by distillation.

The two variants according to the invention are explained in detail below. Various embodiments within a variant can be combined with one another at will, provided that the opposite cannot be inferred by the person skilled in the art from the context.

Variant 1

As a function of the purity of the available fresh benzene and the purity of the recycled benzene (d.2), the two are mixed in a ratio such that the requirements according to the invention of the resulting mixed stream (i.e. of the feed benzene (a.1)) are met in relation to the content of aliphatic organic compounds. The content of aliphatic organic compounds in the feed benzene (a.1) is obtained by adding the content of aliphatic organic compounds of the fresh benzene and the recycled benzene, taking into account the quantitative ratio of these two streams. The higher the content of aliphatic organic compounds in the recycled benzene, the smaller is the quantity of this stream that can be mixed with the fresh benzene to produce the feed benzene (cf. examples). In particular, if the proportion of aliphatic organic impurities in the recycled benzene (d.2) obtained is relatively high and in addition, during the start-up period, the production plant is not yet running under optimum conditions, it may not be possible for the entire stream (d.2) to be recycled. In variant 1, however, preferably at least 25 wt. %, particularly preferably at least 50 wt. % of the stream (d.2) is always returned into step a). Non-recycled portions of the stream (d.2) are either incinerated, returned back into the process after working up by distillation or preferably placed in intermediate storage in a recycled benzene buffer tank and returned gradually into the process after the start-up period has passed, preferably in such a way that the above-mentioned conditions (maximum permissible aliphatics content in stream (a.1)) are also met after the start-up period. However, it is only absolutely essential for the requirements according to the invention relating to the purity of the feed benzene to be met during the start-up period.
Variant 2

In this variant, only fresh benzene is used during the start-up period. Since this generally meets the purity requirements according to the invention, no particular measures are necessary. Only if, contrary to expectations, the fresh benzene to be used should be of inadequate quality must this be purified before use, preferably by distillation. The recycled benzene (d.2) forming during the start-up period can be treated as described in variant 1 for the non-recycled proportions of the stream (d.2).

The steps of the invention which are the same for the two variants are explained in detail below. Different embodiments can be combined together at will, provided that the opposite cannot be clearly inferred from the context by the person skilled in the art.

Step a) can in principle be performed by any adiabatic nitration processes known from the prior art, provided that the specified boundary conditions relating to the benzene excess and the purity of the feed substances can be maintained with these. For implementing this step of the process according to the invention, a tubular reactor is preferably used, in which several dispersing elements are arranged distributed along the length of the reactor, which ensure a thorough dispersing and mixing of benzene, nitric acid and sulfuric acid. A reactor of this type, and the shape of dispersing elements that can be used, are described for example in EP 0708 076 B1 (FIG. 2) and EP 1 291 078 A2 (FIG. 1). Step a) is preferably implemented in a procedure as described in DE 10 2008 048 713 A1, in particular paragraph [0024].

The phase separation in step b) also takes place by processes which are known per se from the prior art in a separating vessel which is known to the person skilled in the art. The aqueous phase (b.1) substantially comprises (as a result of the formation of water of reaction and by the entrainment of water into the reaction from the nitric acid used) dilute sulfuric acid together with inorganic impurities, and the organic phase (b.2) substantially comprises nitrobenzene together with excess benzene and organic impurities.

The concentrating of the aqueous phase (b.1) in step c) takes place in principle as known from the prior art. The sulfuric acid in the aqueous phase is concentrated in a flash evaporator, by vaporizing water into an area of reduced pressure. With a correct selection of the reaction conditions in the adiabatic nitration of benzene with mixed acid, such strong heating of the sulfuric acid-comprising aqueous phase (b.1) is achieved with the heat of reaction from the exothermic reaction that it is simultaneously possible to re-establish in the flash evaporator the concentration and temperature of the sulfuric acid-comprising aqueous phase which this had on entering the reactor chamber before the reaction with benzene and nitric acid, i.e. (c.1) corresponds to (a.2) in terms of temperature and concentration. This is described in EP 2 354 117 A1, in particular paragraph [0045].

The work-up of the organic phase (b.2) in step d) takes place in principle as known from the prior art. A preferred method is described below:

The organic phase (b.2), which generally still comprises traces of acid, is washed with an aqueous washing liquid in one to two washes, preferably one wash, and then separated from the acidic aqueous phase by phase separation (after each individual wash in the case of several washes). In this procedure, the acid residues comprised by the crude nitrobenzene (b.2) are washed out; this process step is therefore also referred to as an acid wash. This step is adequately known from the prior art and is therefore only outlined briefly here. To carry out this acid wash, aqueous streams obtained during operation are preferably recycled. (Step d(i).)

The organic phase thus obtained is then washed in one to two, preferably one, alkaline wash(es) with an aqueous solution of a base, preferably selected from the group consisting of sodium hydroxide, sodium carbonate and sodium hydrogen carbonate, and then separated from the alkaline washing water by phase separation (after each individual wash in the case of several washes). Sodium hydroxide solution is particularly preferably used as the aqueous base solution. This step is adequately known from the prior art and is therefore only outlined briefly here. The pH value of the sodium hydroxide solution used and its mass ratio to the organic phase are adjusted so that acidic impurities (e.g. nitrophenols formed as by-products and acid residues not completely removed in step b)) are largely to completely, preferably completely, neutralised in step c). The subsequent work-up of the alkaline waste water can take place by the processes of the prior art, e.g. according to EP 1 593 654 A1 and EP 1 132 347 A2. (Step d(ii).)

The organic phase thus obtained is finally washed in at least one, preferably two to four, particularly preferably two to three, most particularly preferably two, neutral wash(es) with water and then separated from the aqueous phase by phase separation (after each individual wash in the case of several washes). This can, in principle, take place by any of the processes that are conventional in the prior art. As washing water, preferably deionised water (DI water), particularly preferably a mixture of DI water and steam condensate (i.e. a condensate of water vapour which was obtained by heat exchange of water with any exothermic process steps) and most particularly preferably steam condensate is used. A method is preferred in which, in the last neutral wash, electrophoresis is used (cf. WO 2012/013678 A2). (Step d(iii).)

The washed nitrobenzene is finally freed from dissolved water, unreacted benzene and any organic impurities by a further work-up. This work-up preferably takes place by distillation, the vapours of water and benzene and any organic impurities being expelled overhead. The vapours are cooled and transported into a separating vessel. Water settles out in the bottom phase and is separated off. Benzene and low boilers are found in the top phase, which are supplied back to the reaction as recycled benzene (d.2). A rectifying column is preferably used as the distillation apparatus. The bottom product of the distillation, optionally after a further distillation in which nitrobenzene is obtained as distillate (i.e. as head or sidestream product), is supplied to further applications (such as hydrogenation to form aniline) as pure nitrobenzene (d.1). (Step d(iv).)

By means of the methods according to the invention, the following advantages are obtained for the start-up procedures of adiabatic nitration:

i) The reaction mixture heats up more rapidly, because the desired conversion is reached more rapidly. As a result, it is possible to work with less steam, and the reaction-supporting use of steam can be omitted earlier.

ii) The benzene conversions are optimal and only the excess quantity of benzene over the theoretical quantity, but not further benzene which is present as a result of incomplete reaction, form a load in the work-up in step d).

iii) The formation of by-products in the reaction, such as picric acid and nitrogen oxides (NOx), is minimised because a benzene excess of preferably 2.0% to 20%, particularly preferably of 5.0% to 10% of the theoretical value is always used.

iv) In the so-called "acid wash", the removal of acid residues from the crude product is improved because the phase separation runs more efficiently after the wash as a result of reduced outgassing of organic aliphatic compounds. In addition, the risk of the occurrence of a stable emulsion, which can be separated into two phases only with difficulty, is reduced.

v) The absence of aliphatic organic impurities during the start-up of the nitration of benzene additionally has the advantage that the hydraulic loading in the reaction is lower and therefore the reaction can be ramped up to the target load more rapidly.

Thus, the process according to the invention, by using feed benzene (a.1) with a content of aliphatic organic compounds of less than 1.5 wt. %, preferably of less than 0.50 wt. %, particularly preferably of less than 0.20 wt. %, most particularly preferably of less than 0.10 wt. %, based in each case on the total mass of (a.1), allows a technically trouble-free start-up of the adiabatic nitration of benzene and subsequent work-up of the resulting crude nitrobenzene without stoppage periods and with immediate high quality of the end product.

EXAMPLES

Content data in ppm or % are proportions by mass, based on the total mass of the respective substance (stream). Analytical values were determined by gas chromatography unless otherwise specified.

General Conditions for the Production of Nitrobenzene in a Production Plant which has been Run in (i.e. after the Start-Up Period t has Passed)
(See FIG. 1)

A reactor (1) is supplied with a sulfuric acid (11), a nitric acid (12), a fresh benzene (13) and a recycled benzene stream (21). A 5 to 10% excess of benzene, based on nitric acid, is used. The quantity of recycled benzene depends on this excess and the quality of the feed benzene. After complete conversion of the nitric acid with the benzene to form nitrobenzene with adiabatic reaction management, the reaction product (14) which is now hot, at about 130° C., is fed into phase separation apparatus (2), in which the reaction product (14) breaks down into an organic phase ((15),=crude nitrobenzene, comprising benzene and low boilers together with nitrobenzene) and an aqueous phase ((16),=waste acid, comprising small proportions of nitrobenzene and benzene together with sulfuric acid). The aqueous phase (16), mainly encompassing sulfuric acid, is subjected to flash evaporation of water in the evaporator (3) by a sudden reduction in pressure and is concentrated in this way. The concentrated sulfuric acid (17) is stored in the sulfuric acid tank (4) to be used again. After separation in the phase separation apparatus, the crude nitrobenzene (15) is cooled to about 50° C. in the crude nitrobenzene cooler (5) and fed into the wash (6). The stream of purified crude nitrobenzene (18) thus obtained, which has been largely freed of nitrophenols and salts, is reheated and freed from water, benzene and other low boilers, which are separated off overhead (19), in a distillation column (7), as a result of which dried pure nitrobenzene (20) is obtained and stored in tank (8). The condensed head product (19) of the distillation column (7) is fed to phase separation apparatus (9), in which the head product breaks down into an organic phase ((21), comprising benzene and low boilers) and an aqueous phase (22). The organic phase (21) is stored temporarily in a buffer tank (10) and from there, as already described above, is returned into the inlet of the reactor (1) for reaction.

Nitrobenzene produced in this way typically has a purity of approx. 99.96% (GC), a residual benzene content of 0.0028% (GC), a content of 1,3-dinitrobenzene of 0.0273% (GC) and a nitrophenol content of <5 ppm (HPLC). Furthermore, the nitrobenzene has a water content of 0.0079% (Karl-Fischer).

General Conditions for the Start-Up of an Adiabatic Nitrobenzene Process
(See FIG. 1)

The sulfuric acid circulating pump is started up, and sulfuric acid from the sulfuric acid tank (4) is fed into the reactor (1) and then runs over into the phase separation apparatus (2) and from there into the flash evaporator (3), finally arriving back in the sulfuric acid tank (4). In order to take care of the sulfuric acid circulating pumps used in the nitration reaction, while the plant is warming up, traces of nitric acid are always added to the sulfuric acid in order to passivate the sulfuric acid circulating pump and to prevent the pump from being destroyed by corrosion. In a continuous operating mode, the sulfuric acid is heated to a temperature of 101° C. with indirect steam. The pressure in the flash evaporator is reduced. To start up the nitration, a benzene stream (comprising 13 (fresh benzene) and optionally 21 (recycled benzene)) is fed simultaneously with the nitric acid stream (12) to the reactor inlet, where the nitration begins with the dispersion of the feed substances. In order to reach the nominal capacity of the plant ($M'_{target}$), the process is initially started with smaller mass flows of benzene and nitric acid (in examples 1 to 4, the plant was started with 50% of the nominal capacity, which corresponded to a production output of 30 t/h (nitrobenzene)). These mass flows are then increased during a start-up period t to the nominal load. The ramping up of the plant can be configured manually or with an automatic start-up. In the event that the process is operated during the start-up period only with fresh benzene (variant 2) or with fresh benzene and a reduced quantity of recycled benzene, an additional quantity of fresh benzene is added as the benzene excess. The plant was ramped up to the nominal load as quickly as possible in each case, ensuring that complete conversion of the nitric acid was achieved.

TABLE 1

Comparison of the results from the examples

| Example | Benzene excess | Aliphatics content during the start-up period t | | | Consumption of 6 bar steam | Start-up period |
| --- | --- | --- | --- | --- | --- | --- |
| | | Fresh benzene | Recycled benzene | Feed benzene | | |
| 1 (comparison) | 5.565% | 788 ppm | 48% | 4.43527% | 4 t/h | The nitration did not start |
| 2 (comparison) | 5.612% | 993 ppm | 31% | 2.38824% | 3.1 t/h | 4 h |
| 3 (according to the invention, variant 1) | 6.502% | 975 ppm | 19% | 1.49768% | 1.4 t/h | 2 h |

TABLE 1-continued

Comparison of the results from the examples

Aliphatics content during the start-up period t

| Example | Benzene excess | Fresh benzene | Recycled benzene | Feed benzene | Consumption of 6 bar steam | Start-up period |
|---|---|---|---|---|---|---|
| 4 (according to the invention, variant 2) | 5.896% | 1045 ppm | without recycled benzene during t | 0.1045% | 0.3 t/h | 2 h |

As shown by the examples, with extremely high aliphatics contents in the feed benzene the reaction can no longer be started up (example 1). However, even if the aliphatics content in the feed benzene is reduced as far as in example 2, a very long start-up period of 4 h and an increased input of steam are still necessary to achieve complete conversion of nitric acid, and thus to avoid the formation of $NO_x$ and by-products such as picric acid. By contrast, with the procedure according to the invention, the start-up period and the steam requirements are significantly reduced.

The invention claimed is:

1. A continuous process for the production of nitrobenzene by nitration of benzene, comprising:
   a) reacting a benzene-comprising stream (a.1), which comprises at least 90 wt. % benzene, based on the total mass of (a.1), in a reactor with a mixture of sulfuric acid (a.2) and nitric acid (a.3) under adiabatic conditions, wherein benzene is used in a stoichiometric excess based on nitric acid (a.3), wherein the quantity M' of the benzene-comprising stream (a.1) supplied to the reactor per hour is increased within a period from the beginning of the nitration until a preset target value for M' is reached,
   b) separating the process product obtained in step a) into an aqueous phase comprising sulfuric acid (b.1) and an organic phase comprising nitrobenzene (b.2),
   c) concentrating the aqueous phase (b.1) obtained in step b) by evaporation of water to form an aqueous phase (c.1) with an increased sulfuric acid concentration compared with (b.1), wherein the phase (c.1) is partially to completely returned into step a) and used as a component of (a.2), and
   d) working up the organic phase (b.2) obtained in step b) to form pure nitrobenzene (d.1), wherein a benzene-comprising stream (d.2) is obtained, wherein the stream (d.2) is partially to completely returned into step a) and used as a component of (a.1), the recirculation of (d.2) already taking place during the period t,
   wherein
   at least during the period t only a benzene-comprising stream (a.1) having a content of aliphatic organic compounds of less than 1.5 wt. %, based on the total mass of (a.1), is supplied to the reactor.

2. A continuous process for the production of nitrobenzene by nitration of benzene, comprising:
   a) reacting a benzene-comprising stream (a.1), which comprises at least 90 wt. % benzene, based on the total mass of (a.1), in a reactor with a mixture of sulfuric acid (a.2) and nitric acid (a.3) under adiabatic conditions, wherein benzene is used in a stoichiometric excess based on nitric acid (a.3), wherein the quantity M' of the benzene-comprising stream (a.1) supplied to the reactor per hour is increased within a period from the beginning of the nitration until a preset target value for M' is reached,
   b) separating the process product obtained in step a) into an aqueous phase comprising sulfuric acid (b.1) and an organic phase comprising nitrobenzene (b.2),
   c) concentrating the aqueous phase (b.1) obtained in step b) by evaporation of water to form an aqueous phase (c.1) with an increased sulfuric acid concentration compared with (b.1), wherein the phase (c.1) is partially to completely returned into step a) and used as a component of (a.2), and
   d) working up the organic phase (b.2) obtained in step b) to form pure nitrobenzene (d.1), wherein a benzene-comprising stream (d.2) is obtained,
   wherein
   at least during the period t only a benzene-comprising stream (a.1) having a content of aliphatic organic compounds of less than 1.5 wt. %, based on the total mass of (a.1), is supplied to the reactor and that only after the period t has passed is the benzene-comprising stream (d.2) obtained in step d) partially to completely returned into step a) and used as a component of (a.1).

3. The process according to claim 1, in which the aliphatic organic compounds are selected from the group consisting of cyclohexane, heptane, methylcyclohexane, bicycloheptane, isomers of dimethylcyclopentane, ethylcyclopentane, pentane, cyclopentane and 2-methylhexane.

4. The process according to claim 1, in which at least 25 wt. % of the stream (d.2) is always returned into step a).

5. The process according to claim 1, in which benzene is used in step a) in an excess of 2.0% to 20% of the theoretical value.

6. The process according to claim 1, in which the benzene-comprising stream (d.2) encompasses 40.0 wt. % to 99.9 wt. % benzene, based on the total mass of (d.2).

7. The process according to claim 2, in which the aliphatic organic compounds are selected from the group consisting of cyclohexane, heptane, methylcyclohexane, bicycloheptane, isomers of dimethylcyclopentane, ethylcyclopentane, pentane, cyclopentane and 2-methylhexane.

8. The process according to claim 3, in which at least 25 wt. % of the stream (d.2) is always returned into step a).

9. The process according to claim 2, in which benzene is used in step a) in an excess of 2.0% to 20% of the theoretical value.

10. The process according to claim 2, in which the benzene-comprising stream (d.2) encompasses 40.0 wt. % to 99.9 wt. % benzene, based on the total mass of (d.2).

* * * * *